United States Patent
Cho et al.

(10) Patent No.: US 9,138,488 B2
(45) Date of Patent: Sep. 22, 2015

(54) POLYSORBITOL-BASED OSMOTICALLY ACTIVE TRANSPORTER AND GENE THERAPY USING SAME

(75) Inventors: Myung Haing Cho, Seoul (KR); Chong Su Cho, Seoul (KR)

(73) Assignee: SNU R&DB FOUNDATION, Seoul (KR)

( * ) Notice: Subject to any disclaimer, the term of this patent is extended or adjusted under 35 U.S.C. 154(b) by 43 days.

(21) Appl. No.: 14/007,064

(22) PCT Filed: Aug. 12, 2011

(86) PCT No.: PCT/KR2011/005955
§ 371 (c)(1),
(2), (4) Date: Dec. 6, 2013

(87) PCT Pub. No.: WO2012/133997
PCT Pub. Date: Oct. 4, 2012

(65) Prior Publication Data
US 2014/0348777 A1    Nov. 27, 2014

(30) Foreign Application Priority Data
Mar. 25, 2011    (KR) .................. 10-2011-0027201

(51) Int. Cl.
| A61K 48/00 | (2006.01) |
| A61K 9/00 | (2006.01) |
| A61K 31/047 | (2006.01) |
| C12N 15/87 | (2006.01) |
| C08G 63/685 | (2006.01) |
| C08G 63/91 | (2006.01) |

(52) U.S. Cl.
CPC ............ *A61K 48/0041* (2013.01); *A61K 9/0004* (2013.01); *A61K 31/047* (2013.01); *C08G 63/685* (2013.01); *C08G 63/91* (2013.01); *C12N 15/87* (2013.01); *Y10T 428/2982* (2015.01)

(58) Field of Classification Search
CPC ... A61K 48/0041; C08G 63/685; C08G 63/91
USPC .................... 127/30, 33; 424/78.17; 428/402; 525/54.2; 528/392; 536/18.7, 29.1, 55; 564/278
See application file for complete search history.

(56) References Cited

U.S. PATENT DOCUMENTS

| 7,572,843 B2 * | 8/2009 | Renz et al. ..................... 523/160 |
| 2005/0020729 A1 * | 1/2005 | Renz et al. ..................... 523/160 |

FOREIGN PATENT DOCUMENTS

| KR | 10-2003-0096380 A |  | 11/2003 |  |
| KR | 10-2003-0096380 |  * | 12/2003 | ............... A61K 9/70 |

(Continued)

OTHER PUBLICATIONS

International Search Report, PCT/KR2011/005955, dated Mar. 23, 2012, 4 pages.

(Continued)

*Primary Examiner* — Jane C Oswecki
(74) *Attorney, Agent, or Firm* — Lathrop & Gage LLP; Brian C. Trinque; Jana A. Lewis

(57) ABSTRACT

The present invention relates to a biodegradable polysorbitol-based osmotically active transporter (PSOAT) and gene therapy using the same as a gene carrier. The biodegradable polysorbitol-based osmotically active transporter (PSOAT) of the present invention includes a sorbitol skeleton, which imparts an osmotic pressure to the cell membrane to improve membrane permeability, thereby exhibiting remarkably improved transfection efficiency. Further, the polysorbitol-based osmotically active transporter of the present invention exhibits high DNA binding ability, effectively protects DNA from nuclease, exhibits physicochemical properties suitable for use as a gene carrier, and has very low cytotoxicity in vitro and in vivo, thereby capable of being used as a gene carrier for gene therapy.

21 Claims, 12 Drawing Sheets

(56) References Cited

FOREIGN PATENT DOCUMENTS

| KR | 10-2006-0025711 | * | 3/2006 | ............ C12N 11/08 |
| KR | 100806601 B1 | | 3/2006 | |
| KR | 10-2009-0040289 | * | 4/2009 | ............... A61K 9/08 |
| KR | 10-2009-0040289 A | | 4/2009 | |

OTHER PUBLICATIONS

Written Opinion, PCT/KR2011/005955, dated Mar. 23, 2012, 5 pages.

* cited by examiner

POLYSORBITOL-BASED OSMOTICALLY ACTIVE TRANSPORTER AND GENE THERAPY USING SAME

RELATED APPLICATIONS

This application is a 35 U.S.C. §371 filing of International Application No. PCT/KR2011/005955, filed Aug. 12, 2011; which claims priority to Korean Patent Application No. 10-2011-0027201, filed on Mar. 25, 2011. The entire contents of each are incorporated herein by reference.

TECHNICAL FIELD

The present invention relates to a biodegradable polysorbitol-based osmotically active transporter (PSOAT) and gene therapy using the same as a gene carrier. The biodegradable polysorbitol-based osmotically active transporter of the present invention has osmotic activity due to a sorbitol skeleton and a proton sponge effect due to a polyethyleneimine (PEI) skeleton, and thus it induces efficient intracellular influx to show a remarkably improved transfection efficiency and a high DNA-binding ability, and effectively protects DNA from nuclease and exhibits very low cytotoxicity and physicochemical properties that make it suitable for use as a gene carrier. Accordingly, the biodegradable polysorbitol-based osmotically active transporter of the present invention can be used as a safe and effective gene carrier for gene therapy.

BACKGROUND ART

Gene therapy is a method of treating diseases by conveying a therapeutic gene into a target organ in the body and by inducing intracellular expressions of new proteins, and is aimed at treating and eliminating not just the symptoms but the cause of disease. Gene therapy has an excellent selectivity, compared with other treatment methods using general drugs, and can be applied for a long period of time because it improves the treatment rate and time of diseases that are hard to treat. Because using DNA as the therapeutic gene is prone to enzymatic hydrolysis in the body and its transfection efficiency is low, it is essential to develop a gene carrier that safely delivers the therapeutic gene into the target cells to achieve a high expression efficiency for effective gene therapy.

A gene carrier must be slightly toxic or non-toxic, and have an ability to deliver the gene into the target cells with selectivity and efficacy. Such gene carriers can be largely divided into viral and non-viral vectors. Up to now, a viral vector having a high transfection efficiency has been used as the gene carrier in clinical trials. However, there are many limitations in the application of viral vectors such as retrovirus, adenovirus, and adeno-associated virus in the human body, because of their complex preparation, safety problems including immunogenicity, risk of infection, inflammation induction, and non-specific DNA insertion, and the limited size of loading DNA. Thus, much attention has been paid to non-viral vectors as an alternative to the viral vectors.

The non-viral vectors have the many advantages of being administered repeatedly with minimal immune response, targeting specific cells, being stable in storage, and being easily produced in large quantities. Examples of the non-viral vectors include cationic liposome-based N-[1-(2,3-dioleyloxy)propyl]-N,N,N-trimethylammonium chloride (DOTMA), alkylammonium, cationic cholesterol derivatives, gramicidin or the like.

Of the non-viral vectors, cationic polymers have recently attracted much attention, because they can form a complex with negatively charged DNA via an ionic bond. These cationic polymers includes poly-L-lysine (PLL), poly(4-hydroxy-L-proline ester), polyethyleneimine (PEI), poly[α-(4-aminobutyl)-L-glycolic acid], polyamidoamine dendrimer, poly[N,N'-(dimethylamino)ethyl]methacrylate (PD-MAEMA) or the like. They condense DNA into nanoparticles to protect DNA from enzymatic degradation, and facilitate its cellular uptake to enhance endosomal escape. Compared to viral vectors, most non-viral vectors have the advantages of biodegradability, low toxicity, non-immunogenicity, ease of use or the like, but there are still present the problems of relatively low transfection efficiency, limited particle size or the like.

In particular, most of the cationic polymers used as non-viral vectors exhibit a high transfection efficiency in vitro under a low-serum environment, but the cationic polymer/gene complex shows a remarkably low transfection efficiency due to a variety of factors present in the serum under in vivo environments, resulting in a poor intracellular influx of the gene. This is attributed to the non-specific interaction of excessive positive charges on the surface of the cationic polymer/gene complex with the plasma proteins and blood components in vivo. That is, the transfection efficiency of the cationic polymer is remarkably reduced in the presence of a large amount of serum in vivo, not under serum-free or very low serum conditions in vitro. When applied as it is in the body, the cationic polymer can be agglomerated and accumulated in the lung, liver and spleen, and also removed by opsonization via the reticuloendothelial system. Therefore, therapeutic applications of the cationic polymers are very limited. Polyethyleneimine (PEI), one of the most widely investigated non-viral vectors, also has the drawbacks of very low transfection efficiency in vivo, high cytotoxicity, and low gene expression efficiency due to low blood compatibility.

Therefore, there is an urgent need to develop a gene carrier having an enhanced transfection efficiency while maintaining the advantages of the conventional non-viral vectors.

Accordingly, the present inventors have endeavored to develop a gene carrier having low cytotoxicity and high transfection efficiency. As a result, they found that a polysorbitol-based osmotically active transporter (PSOAT) prepared by Michael addition between polyethyleneimine (PEI) and a sorbitol-based derivative shows very low cytotoxicity in vitro and in vivo, and has an osmotic activity due to a sorbitol skeleton and a proton sponge effect due to a polyethyleneimine (PEI) skeleton so as to exhibit a remarkably improved transfection efficiency, and thus the polysorbitol-based osmotically active transporter can be used as a gene carrier for gene therapy, thereby completing the present invention.

DISCLOSURE

Technical Problem

An object of the present invention is to provide a biodegradable polysorbitol-based osmotically active transporter that exhibits no cytotoxicity as a gene carrier and has a remarkably improved transfection efficiency.

Another object of the present invention is to provide a method for preparing the biodegradable polysorbitol-based osmotically active transporter.

Still another object of the present invention is to provide a gene delivery complex that is prepared by binding a therapeutic gene to the biodegradable polysorbitol-based osmotically active transporter.

Still another object of the present invention is to provide a pharmaceutical composition for gene therapy, including the gene delivery complex as an active ingredient.

Technical Solution

In one aspect to achieve the above objects, the present invention provides a biodegradable polysorbitol-based osmotically active transporter (PSOAT) that is a copolymer of polyethyleneimine (PEI) and a sorbitol-based derivative.

The biodegradable polysorbitol-based osmotically active transporter (PSOAT) according to the present invention can be prepared by Michael addition of polyethyleneimine and the sorbitol-based derivative.

As used herein, the term "polyethyleneimine (PEI)" refers to a cationic polymer having primary, secondary, and tertiary amino groups and a molecular weight of 1,000 to 100,000 g/mol. Polyethyleneimine effectively condenses plasmid DNA into colloidal particles, and has a high transfection efficiency due to a pH-buffering capacity, thereby effectively delivering a gene into a variety of cells in vitro and in vivo. In the present invention, polyethyleneimine may have a linear form represented by the following Chemical Formula 1 or a branched form represented by the following Chemical Formula 2. Considering cytotoxicity, its molecular weight should be a low molecular weight, and preferably 50 to 10,000 Da. Polyethyleneimine is dissolved in water, alcohol, glycol, dimethylformamide, tetrahydrofuran, esters or the like, and is not dissolved in high-molecular weight hydrocarbons, oleic acid, and diethyl ether.

[Chemical Formula 1]

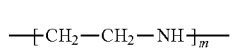

[Chemical Formula 2]

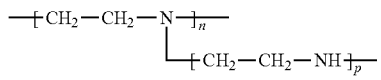

In the present invention, polyethyleneimine functions as a Michael donor in a Michael addition with sorbitol-based derivative, and the resulting copolymer thus synthesized functions to impart a high transfection efficiency, low cytotoxicity and a proton sponge effect.

As used herein, the term "sorbitol-based derivative" refers to any compound having a sorbitol sugar alcohol skeleton and also having an acrylate group or a methacrylate group in the sugar alcohol skeleton, and any compound can be used without limitation, as long as it is able to modify polyethyleneimine to impart a sorbitol skeleton to the final copolymer. In the present invention, the sorbitol-based derivative functions as a Michael acceptor in a Michael addition with polyethyleneimine, and functions to impart hydrophilicity, biodegradability and osmotic activity to the resulting synthesized copolymer, and to improve stability in the serum and after freeze-drying.

Examples of the sorbitol-based derivative suitable to the present invention may include sorbitol diacrylate (SDA), sorbitol dimethacrylate (SDM), sorbitol triacrylate (STA), sorbitol trimethacrylate (STM), sorbitol tetraacrylate (STEA), sorbitol tetramethacrylate (STEM), sorbitol pentacrylate (SPA), sorbitol pentamethacrylate (SPM) or the like, and preferably, sorbitol dimethacrylate (molecular weight of 318 Da) represented by the following Chemical Formula 3.

[Chemical Formula 3]

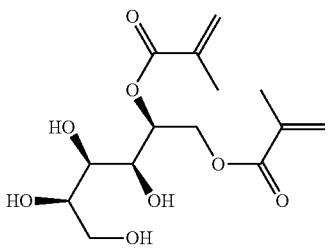

As used herein, the term "polysorbitol-based osmotically active transporter (PSOAT)" refers to a copolymer that is formed by Michael addition between an amine group of polyethyleneimine and an acrylate group or a methacrylate group of the sorbitol-based derivative. The polysorbitol-based osmotically active transporter (PSOAT) of the present invention has a repeated structure of 0.9 to 0.1 molecule of polyethyleneimine binding to 0.1 to 0.9 molecule of sorbitol-based derivative. The polysorbitol-based osmotically active transporter (PSOAT) of the present invention has an osmotic activity due to a sorbitol skeleton and a proton sponge effect due to a polyethyleneimine (PEI) skeleton, and thus it induces efficient intracellular influx to show remarkably improved transfection efficiency and very low cytotoxicity, thereby being useful as a gene carrier for gene therapy. The polysorbitol-based osmotically active transporter (PSOAT) of the present invention preferably has a molecular weight ranging from 1,000 to 100,000 Da for efficient gene delivery. Further, the polysorbitol-based osmotically active transporter (PSOAT) of the present invention preferably has a zeta potential ranging from 1 to 50 mV for efficient gene delivery. When the polysorbitol-based osmotically active transporter (PSOAT) of the present invention exhibits the physicochemical properties within the above range, it can be effectively internalized as a gene carrier into the endosome of the cells.

In the specific embodiment of the present invention, the polysorbitol-based osmotically active transporter (PSOAT) according to the present invention can be represented by the following Chemical Formula 4.

[Chemical Formula 4]

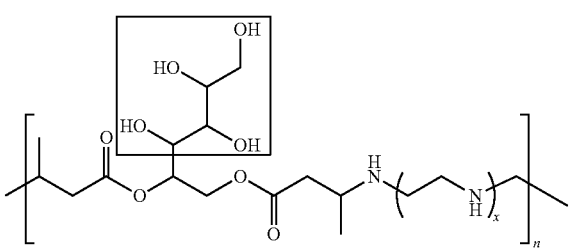

wherein x is an integer of 1 to 200, and n is an integer of 1 to 500.

The polysorbitol-based osmotically active transporter (PSOAT) of Chemical Formula 4 is a copolymer that is prepared by Michael addition between the amine group of linear polyethyleneimine represented by Chemical Formula 1 and the acrylate or methacrylate group of sorbitol dimethacrylate represented by Chemical Formula 3.

In another aspect, the present invention provides a method for preparing the biodegradable polysorbitol-based osmotically active transporter (PSOAT), including the step of preparing a copolymer by Michael addition between polyethyleneimine and the sorbitol-based derivative.

The preparation method of the present invention may include the steps of:

1) dissolving polyethyleneimine and the sorbitol-based derivative in reaction solvents, respectively;

2) adding the sorbitol-based derivative solution to the polyethyleneimine solution to perform Michael addition; and 3) separating the copolymer formed from the reactants to obtain the polysorbitol-based osmotically active transporter (PSOAT).

In detail, step 1) is a step of dissolving polyethyleneimine and the sorbitol-based derivative in each reaction solvent to prepare reaction solutions for Michael addition between the polyethyleneimine as a Michael donor and the acrylate or methacrylate-containing sorbitol-based derivative as a Michael acceptor. The sorbitol-based derivative suitable to the present invention may be any one without limitation as long as it includes an acrylate group or a methacrylate group. Examples of the sorbitol-based derivative may include sorbitol diacrylate (SDA), sorbitol dimethacrylate (SDM), sorbitol triacrylate (STA), sorbitol trimethacrylate (STM), sorbitol tetraacrylate (STEA), sorbitol tetramethacrylate (STEM), sorbitol pentaacrylate (SPA), sorbitol pentamethacrylate (SPM) or the like. In the preferred embodiment of the present invention, sorbitol dimethacrylate (molecular weight of 318 Da) is used. The polyethyleneimine suitable to the present invention may have a linear or branched form having a low molecular weight of 50 to 10,000 Da. As the reaction solvent usable in the present invention, any solvent can be properly selected as long as it is able to dissolve polyethyleneimine and the sorbitol-based derivative while it does not react with or decompose them. Examples of the reaction solvent may include dimethyl sulfoxide, methyl alcohol anhydrous, ethyl alcohol, dimethylformamide, dioxane or the like.

Step 2) is a step of adding the sorbitol-based derivative solution to the polyethyleneimine solution prepared in step 1) under stirring to perform Michael addition between the amine group of polyethyleneimine and the acrylate group of the sorbitol-based derivative. In this step, Michael addition is preferably performed at 40 to 100° C. for 1 to 24 hours. In the Michael addition according to the present invention, a reaction molar ratio (N/P ratio) of polyethyleneimine and sorbitol-based derivative is preferably in the range of 1:0.1 to 1:10, and preferably 1:1. In the preferred embodiment of the present invention, 1 M sorbitol dimethacrylate reaction solution was slowly added to 4 M polyethyleneimine reaction solution under stirring at 4° C. for 2 hours, and then reacted at 80° C. for 12 hours to perform Michael addition.

Step 3) is a step of separating the copolymer formed by Michael addition of step 2). In the preferred embodiment of the present invention, the obtained reactant was subjected to dialysis (MWCO=3500) against distilled water at 4° C. for 24 hours to separate the polysorbitol-based osmotically active transporter (PSOAT). The polysorbitol-based osmotically active transporter (PSOAT) thus separated can be freeze-dried and stored at −25° C., and the freeze-drying can be performed by a freeze-drying method or using a freeze dryer typically used. As a result, a viscous biodegradable polysorbitol-based osmotically active transporter (PSOAT), from which by-products are removed, can be obtained.

With respect to the polysorbitol-based osmotically active transporter (PSOAT) prepared according to the method of the present invention, the result of gel filtration chromatography showed that the molecular weight of PSOAT copolymer was 11,180 Da, and the result of 1H NMR showed that the chemical compositions of polyethyleneimine and sorbitol dimethacrylate in the copolymer were 65.88 and 34.12 mol %, respectively (see Table 1). Further, the proton peaks of polyethyleneimine and sorbitol dimethacrylate in the obtained copolymer were detected at $\delta$=2.22-2.55 ppm and $\delta$=5.8-6.8 ppm, respectively (see FIG. 2), indicating that the polysorbitol-based osmotically active transporter (PSOAT) according to the present invention was effectively synthesized by Michael addition between polyethyleneimine and sorbitol dimethacrylate.

In still another aspect of the present invention, the present invention provides a gene delivery complex prepared by binding a therapeutic gene to the biodegradable polysorbitol-based osmotically active transporter (PSOAT). The type of therapeutic gene to be bound to the biodegradable polysorbitol-based osmotically active transporter (PSOAT) of the present invention is not particularly limited, and any gene that is delivered to the desired target to exert the desired therapeutic effect depending on the purpose is included in the scope of the present invention. For example, the gene that can be delivered in the form of complex with the biodegradable polysorbitol-based osmotically active transporter (PSOAT) of the present invention may include a normal gene of the therapeutic gene associated with the disease, a gene suppressing the target protein expression, a large or small polynucleotide containing an antisense polynucleotide, and any RNA form containing lybozyme or siRNA.

The therapeutic gene that can be bound to the biodegradable polysorbitol-based osmotically active transporter (PSOAT) according to the present invention may include DNA, single-stranded RNA, double-stranded RNA, lybozyme, DNA-RNA hybrid, and antisense DNA (e.g., antisense oligonucleotide), and preferably, siRNA.

For the effective preparation of the gene delivery complex according to the present invention, the therapeutic gene and the polysorbitol-based osmotically active transporter (PSOAT) are preferably reacted at a molar ratio of 1:0.5 to 1:100, and preferably 1:5 to 1:30.

In order to examine condensation capability of the polysorbitol-based osmotically active transporter (PSOAT) according to the present invention for the therapeutic gene, the polysorbitol-based osmotically active transporter and DNA were reacted at various molar ratios. As a result, when the molar ratio is 1:0.5 or more, the gene delivery complex (PSOAT/DNA) of the polysorbitol-based osmotically active transporter and DNA was most effectively formed (see FIG. 3a), DNA in the gene delivery complex was effectively protected from nuclease attack (see FIG. 3b), and the formed gene delivery complex had a spherical compact structure (see FIG. 4a). Further, the gene delivery complex according to the present invention showed a relatively uniform particle size distribution (PDI: 2.5e-003) of 150 to 250 nm in average (see FIG. 4b), indicating that it has a particle size suitable for use as the gene carrier and its surface charge shows a positive zeta potential of 15 to 35 mV (see FIG. 4c), and thus it can effectively bind to the negatively charged cell surface.

Further, in order to examine the transfection efficiency of the polysorbitol-based osmotically active transporter (PSOAT) according to the present invention, it was reacted with DNA at various molar ratios to form the gene delivery complexes (PSOAT/DNA), and then their transfection efficiency was examined by luciferase activity assay. As a result, when the moral ratio of DNA and polysorbitol-based osmotically active transporter (PSOAT) was increased from 1:5 to 1:20, the transfection efficiency of the gene delivery complex was increased, but the similar levels of high transfection efficiency were observed at the molar ratio of 1:30 or more. In particular, the gene delivery complex of the present invention showed several-fold to several hundred-fold higher transfection efficiency than the polyethyleneimine (PEI 25K)-treated group as a control group (see FIGS. 5a to 5c), and stably maintained high transfection efficiency in the presence of serum, compared to the lipofectamine having a rapidly reduced transfection efficiency (see Table 6). These results indicate that the polysorbitol-based osmotically active transporter (PSOAT) of the present invention has excellent DNA binding ability, and effectively forms the nano-sized gene delivery complex, and thus exhibits a high transfection efficiency and stably maintains the high transfection efficiency in the presence of serum, thereby being desirably applied in the body. The high transfection efficiency of the polysorbitol-based osmotically active transporter (PSOAT) according to the present invention is attributed to the buffering capacity of the copolymer.

Therefore, in order to investigate the transfection mechanism of the polysorbitol-based osmotically active transporter (PSOAT) according to the present invention, the buffering capacity of the copolymer was examined using an endosome proton pump inhibitor, bafilomycin A1. As a result, the transfection efficiency of the polysorbitol-based osmotically active transporter (PSOAT) according to the present invention was rapidly reduced after treatment of bafilomycin A1 (see FIG. 7a), indicating that the polysorbitol-based osmotically active transporter (PSOAT) of the present invention can be effectively released from the endosome into the cytoplasm by the proton sponge effect.

Meanwhile, the polysorbitol-based osmotically active transporter (PSOAT) according to the present invention includes the osmotically active sorbitol skeleton, which imparts an osmotic pressure to the cell membrane and makes the cell membrane mild, thereby facilitating cell re-absorption by improved membrane permeability. In order to confirm this, changes in packed cell volume (PCV) by treatment of the PSOAT copolymer of the present invention were measured. As a result, the PSOAT/DNA complex having the sorbitol skeleton was found to reduce PCV in the same manner as that caused by the treatment of pure sorbitol (see FIG. 7b). Further, the effect of the osmotic activity on the transfection efficiency of the polysorbitol-based osmotically active transporter (PSOAT) according to the present invention was analyzed by treatment of an osmotic pressure inhibitor. As a result, as the treatment concentration of the pressure inhibitor was increased, the transfection efficiency of the PSOAT/GL3 complex of the present invention was remarkably reduced (see FIGS. 8a to 8c). These results indicate that the more enhanced transfection efficiency of the polysorbitol-based osmotically active transporter (PSOAT) of the present invention is attributed to the osmotic activity due to the sorbitol skeleton.

Further, cytotoxicity of the polysorbitol-based osmotically active transporter (PSOAT) according to the present invention was examined in various cell lines. As a result, it exhibited remarkably low cytotoxicity, compared to polyethyleneimine (PEI 25K) used as a control group (see FIGS. 9a to 9c).

Further, in order to examine in vitro transfection efficiency of the polysorbitol-based osmotically active transporter (PSOAT) according to the present invention, PSOAT and green fluorescent protein (GFP) gene were mixed at a molar ratio of 20:1 to prepare gene delivery complexes (PSOAT/GFP), which were transfected into cells, followed by flow cytometry. As a result, remarkably increased GFP signals were detected in the group treated with the gene delivery complex (PSOAT/GFP) according to the present invention, compared to the group treated with a complex of polyethyleneimine and GFP (PEI 25K/GFP) as a control group, and no cytotoxicity was observed in all treatment groups (see FIG. 10).

In order to examine in vivo transfection efficiency of the polysorbitol-based osmotically active transporter (PSOAT) of the present invention, the gene delivery complex (PSOAT/GFP) prepared as above was administered to the lungs of normal mice via aerosol, and then GFP signals in the lungs removed from the mice were examined under a fluorescence microscope. As a result, GFP signals were detected in all mice administered with the gene delivery complex (PSOAT/GFP) of the present invention, and in particular, high GFP signals were detected in the mice, compared to mice treated with the complex of polyethyleneimine and GFP (PEI 25K/GFP) (see FIG. 11).

Therefore, the biodegradable polysorbitol-based osmotically active transporter (PSOAT) of the present invention shows high DNA binding ability, and effectively protects DNA from nuclease, and also forms a spherical gene delivery complex having a uniform particle size suitable for use as the gene carrier, and shows very low cytotoxicity in vitro and in vivo and a very high transfection efficiency, thereby being useful as the gene carrier for gene therapy.

Accordingly, in still another aspect of the present invention, the present invention provides a pharmaceutical composition for gene therapy, including the gene delivery complex prepared by binding the therapeutic gene to the biodegradable polysorbitol-based osmotically active transporter (PSOAT) as an active ingredient.

The pharmaceutical composition of the present invention may be administered together with a pharmaceutically acceptable carrier. For oral administration, the pharmaceutical composition may include a binder, a lubricant, a disintegrating agent, an excipient, a solubilizer, a dispersing agent, a stabilizer, a suspending agent, a pigment, a flavor or the like, in addition to the above active ingredient. For injectable formulation, the pharmaceutical composition of the present invention may include a buffer, a preservative, an analgesic, a solubilizer, an isotonic agent, a stabilizer or the like. For topical administration, the composition of the present invention may include a base, an excipient, a lubricant, a preservative or the like.

The composition of the present invention may be prepared in a variety of formulations by mixing with pharmaceutically acceptable carriers as described above. For oral administration, the pharmaceutical composition may be prepared in the form of a tablet, a troche, a capsule, an elixir, a suspension, a syrup, a wafer or the like. The injectable composition may be formulated in unit dosage ample or multi dosage form. It can be also prepared as a solution, a suspension, a tablet, a pill, a capsule, a sustained release formulation or the like.

Meanwhile, examples of the carrier, excipient, and diluent suitable for the formulation may include lactose, dextrose, sucrose, sorbitol, mannitol, xylitol, erythritol, maltitol, starch, acacia, alginate, gelatin, calcium phosphate, calcium silicate, cellulose, methyl cellulose, microcrystalline cellulose, polyvinyl pyrrolidone, water, methylhydroxy benzoate, propylhydroxy benzoate, talc, magnesium stearate, mineral oil or the like. The formulations may further include a filler, an anti-agglutinating agent, a lubricating agent, a wetting agent, a flavoring agent, a preservative or the like.

The pharmaceutical composition of the present invention may be administered via an oral or parenteral route. Examples of the administration route of the pharmaceutical composition according to the present invention may include, but is not limited to, oral, intravenous, intramuscular, intraarterial, intramedullary, intradural, intracardial, transdermal, subcutaneous, intraperitoneal, gastrointestinal, sublingual or topical route. For clinical administration, the pharmaceutical composition of the present invention may be formulated into an appropriate formulation by using the known technology. For example, upon oral administration, the pharmaceutical composition may be mixed with an inactive diluent or edible carrier, sealed in a hard or soft gelatin capsule or pressed into tablets for administration. For the oral administration, the active ingredient may be mixed with an excipient to be used in form of ingestible tablet, buccal tablet, troche, capsule, elixirs, suspension, syrup, wafer or the like. Also, various formations for, for example, injection, parenteral administration or the like may be prepared according to known techniques in the field of this specification or a commonly used technique.

The composition of the present invention is administered in a pharmaceutically effective amount. As used herein, the term "pharmaceutically effective amount" refers to an amount sufficient to treat diseases, at a reasonable benefit/risk ratio applicable to any medical treatment. The effective dosage level may be determined depending on the type and severity of the disease, the activity of the drug, sensitivity to the drug, the time of administration, the route of administration, excretion rate, the duration of treatment, drugs used in combination with the composition, and other factors known in the medical field. The composition of the present invention may be administered alone or in combination with other therapeutic agents, and may be administered sequentially or simultaneously with conventional therapeutic agents. The composition can be administered in a single or multiple dosage form. It is important to administer the composition in the minimum amount that can exhibit the maximum effect without causing side effects, in view of all the above-described factors, this amount can be easily determined by a person skilled in the art.

In the specific embodiment of the present invention, the present invention provides an aerosol formulation of the pharmaceutical composition, which is formulated to deliver the gene delivery complex prepared by binding a therapeutic gene to the polysorbitol-based osmotically active transporter (PSOAT) to a target site via aerosol delivery.

Drug delivery via inhalation is one of non-invasive methods, and in particular, the gene delivery via an aerosol method can be advantageously used in the wide treatment of lung diseases, because the anatomical structure and location of the lung allows immediate non-invasive access, and local application of the gene delivery system is possible without affecting other organs. Therefore, when a gene associated with a lung disease, in particular, lung cancer as a therapeutic gene is bound to the biodegradable polysorbitol-based osmotically active transporter (PSOAT) of the present invention to prepare a gene delivery complex, and it is delivered to the lung via the aerosol method, it is expected to prevent or treat the disease.

The delivery method of the pharmaceutical composition according to the present invention may include oral inhalation and nasal inhalation, a method of using a face mask or an oral tube, and a method of using an oxygen hood for children which has been used for oxygen administration. In general, small particle aerosol is created by an atomization process, and the atomization process is carried out by jet spray.

The pharmaceutical composition of the present invention should be prepared by considering that an aqueous dispersant is prepared to deliver the aerosol to the respiratory tract of an individual or animal. An appropriate administration dose of the aerosol formulation can be easily determined by those skilled in the art without excessive experiment. When used in vivo for targeted gene therapy, the pharmaceutical composition of the present invention is administered to a patient or an animal in a therapeutically effective amount, that is, in an amount of eliminating or ameliorating the corresponding disease by effectively expressing the therapeutic gene. The dose and dosage regimen depend on the type of disease, the characteristics of particular polysorbitol-based copolymer/DNA complex, for example, its therapeutic index, a patient, the patient's disease history, and other factors. Typically, the dose of the pharmaceutical composition according to the present invention may be approximately 0.01 to approximately 0.1 g/body kg. The composition and formulation of the present invention may include a trace amount of additive, for example, a substance improving the isotonicity and chemical stability (e.g., buffer, preservative, etc.).

In still another aspect of the present invention, the present invention provides a method for preventing or treating therapeutic gene-related disease or symptoms, including the step of administering the gene delivery complex, which is prepared by binding the therapeutic gene to the biodegradable polysorbitol-based osmotically active transporter (PSOAT), in a therapeutically effective amount to a subject having a disease or symptoms that can be prevented or treated by delivery of the therapeutic gene.

As used herein, the term "prevention" refers to all of the actions by which the target disease or symptom is restrained or retarded by administration of the gene delivery complex according to the present invention.

As used herein, the term "treatment" refers to all of the actions by which the target disease or symptom have taken a turn for the better or been modified favorably by administration of the gene delivery complex according to the present invention.

As used herein, the term "administration" means introduction of a predetermined active ingredient into a patient by a certain suitable method, and the composition may be administered via any of the common routes, as long as the active ingredient is able to reach a desired tissue. It can be administered intraperitoneally, intravenously, intramuscularly, subcutaneously, intradermally, orally, topically, intranasally, intrapulmonarily and intrarectally, but the present invention is not limited to these exemplified administration modes. Preferably, the composition may be administered in the form of aerosol.

As used herein, the term "subject" means all animals including human, monkey, cattle, horse, sheep, pig, chicken, turkey, quail, cat, dog, mouse, rat, rabbit or guinea pig, but is not limited thereto. In one embodiment, it means a mammal, and in another embodiment, it means human.

As used herein, the term "therapeutically effective amount", used in connection with the active ingredient, means an amount of the biodegradable polysorbitol-based osmotically active transporter being effective for treating or preventing the target disease or symptom.

Advantageous Effects

The biodegradable polysorbitol-based osmotically active transporter (PSOAT) of the present invention includes an osmotically active sorbitol skeleton, which imparts an osmotic pressure to the cell membrane to improve membrane permeability, thereby facilitating cell re-absorption, and thus it exhibits remarkably improved transfection efficiency. Further, the polysorbitol-based osmotically active transporter (PSOAT) of the present invention exhibits high DNA binding ability, effectively protects DNA from nuclease, exhibits physicochemical properties suitable for use as a gene carrier, and very low cytotoxicity in vitro and in vivo, thereby being useful as a gene carrier for gene therapy.

DESCRIPTION OF DRAWINGS

FIGS. 5a to 5c are the result of analyzing the transfection efficiency of the gene delivery complexes (PSOAT/DNA) prepared by reacting the polysorbitol-based osmotically active transporter (PSOAT) of the present invention and DNA at various molar ratios in various cell lines in the serum-free medium (n=3, error bars represent standard deviation), in which FIG. 5a is the result for A549 cell line; FIG. 5b is the result for HeLa cell line; and FIG. 5c is the result for H322 cell line, RLU in Figures is an abbreviation of 'relative light unit' indicating the degree of luminescence;

FIGS. 8a to 8c are the results of examining the effect of osmotic activity on the transfection efficiency of the polysorbitol-based osmotically active transporter (PSOAT) of the present invention, in which FIGS. 8a, 8b and 8c are the results at 1 hour, 2 hours, and 4 hours after treatment of an osmotic pressure inhibitor, respectively;

FIGS. 9a to 9c are the results of examining the cytotoxicity of the polysorbitol-based osmotically active transporter (PSOAT) of the present invention at various concentrations in various cell lines, in which FIG. 9a is the result for A549 cell line; FIG. 9b is the result for HeLa cell line; and FIG. 9c is the result for H322 line;

BEST MODE

Hereinafter, the present invention will be described in more detail with reference to Examples. However, these Examples are for illustrative purposes only, and the invention is not intended to be limited by these Examples.

Example 1

Preparation of Biodegradable Polysorbitol-Based Osmotically Active Transporter

Figure 1:
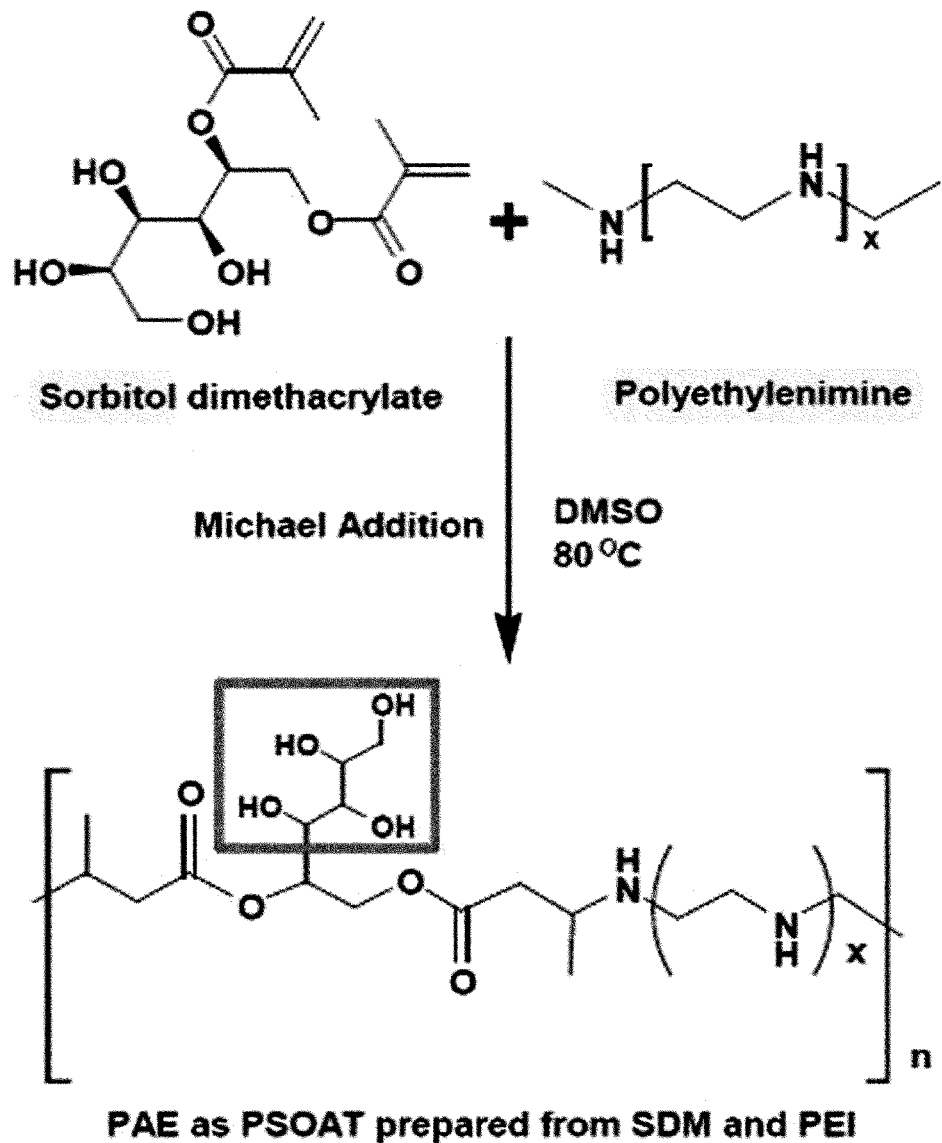
FIG. 1 is a schematic diagram showing a preparation method of the biodegradable polysorbitol-based osmotically active transporter (PSOAT) according to the present invention.

The biodegradable polysorbitol-based osmotically active transporter (PSOAT) according to the present invention was synthesized by Michael addition slightly modified according to the method reported in the literature (Arote R B, et al., Bioconjug. Chem. 2009, 20(12): 2231-41) (FIG. 1).

Briefly, 0.01M low-molecular-weight polyethyleneimine (LMW-PEI) (MW: 423 Da, Sigma-Aldrich) and 0.01M sorbitol dimethacrylate (SDM) (MW: 318.32 Da, Monomer-Polymer & Dajac Labs, Inc.) were dissolved in anhydrous dimethyl sulfoxide at 4° C., respectively. A PEI solution thus prepared was slowly added to an SDM solution prepared under stirring at 4° C. for 2 hours. They were reacted at 80° C. for 12 hours. The copolymer thus obtained was subjected to dialysis against distilled water using a dialysis membrane (Spectra/Por, MWCO=3500) at 4° C. for 24 hours five times to remove unreacted substances. The separated polysorbitol-based osmotically active transporter (PSOAT) was freeze-dried at −20° C.

Figure 2:
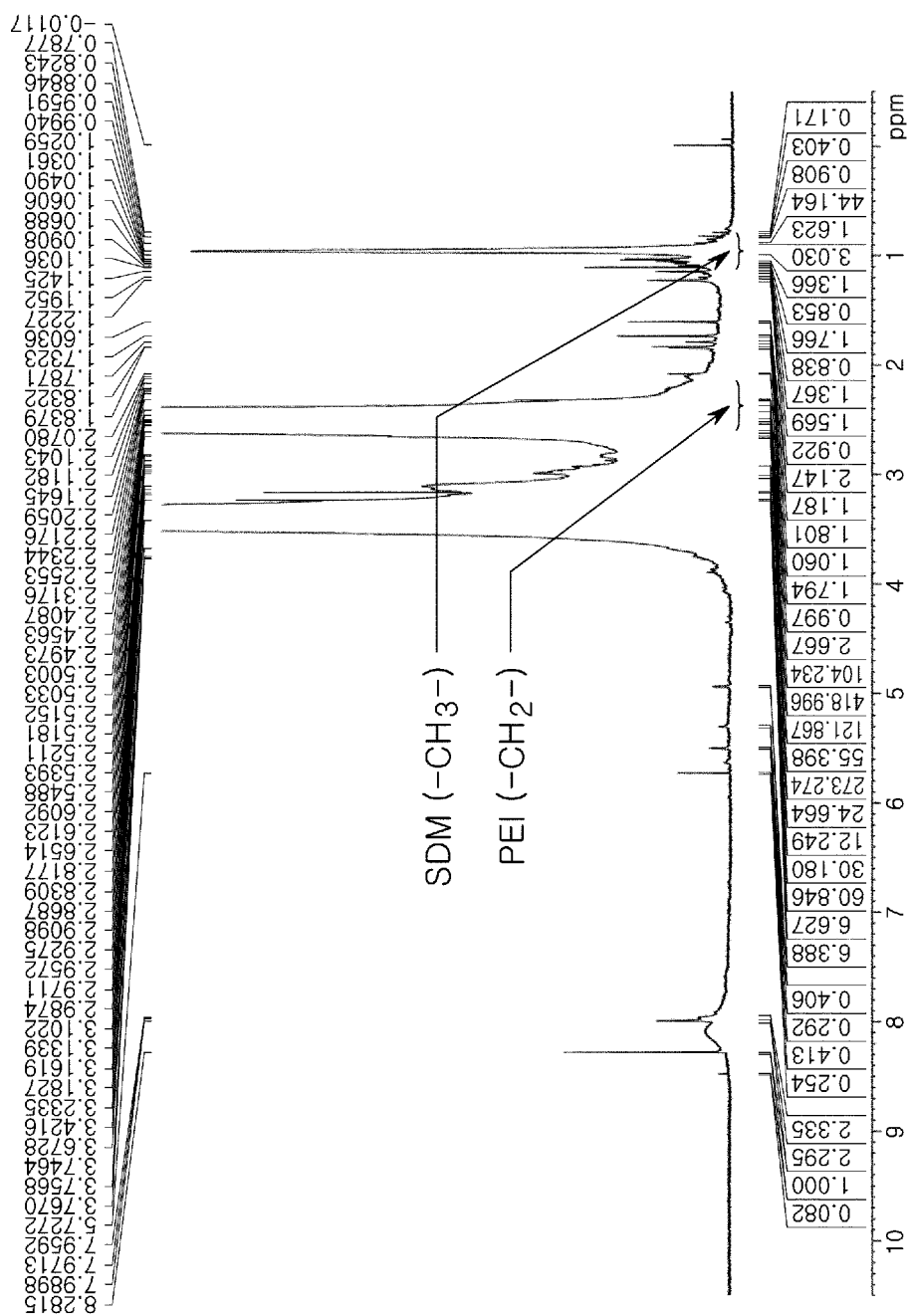
FIG. 2 is the $^1$H-NMR result showing the composition of the polysorbitol-based osmotically active transporter (PSOAT) prepared according to the present invention.

The composition of the polysorbitol-based osmotically active transporter (PSOAT) thus freeze-dried was analyzed by 1H-nuclear magnetic resonance ($^1$H-NMR) (Avance 600, Bruker, Germany). For $^1$H-NMR analysis, the polysorbitol-based osmotically active transporter (PSOAT) was dissolved in distilled water at a concentration of 10 mg/ml. As shown in FIG. 2, the proton peaks of sorbitol dimethacrylate and polyethyleneimine were detected at δ=5.8-6.8 ppm and δ=2.22-

2.55 ppm, respectively. It was found that the copolymer of polyethyleneimine and sorbitol dimethacrylate was effectively synthesized.

The characteristics of the polysorbitol-based osmotically active transporter (PSOAT) thus synthesized are summarized in the following Table 1.

TABLE 1

| Section | Reactant (wt %) | | Molar ratio of SDM:PEI (mol/mol) | PEI composition (mol-%)[a] | SDM composition (mol-%)[a] | molecular weight (Da)[b] |
|---|---|---|---|---|---|---|
| | SDM | PEI | | | | |
| SDM:PEI 423 | 318.32 | 423 | 1:1 | 65.88 | 34.12 | 11,180 |

[a]1H NMR measured values
[b]gel filtration chromatography (GPC) measured values Example 2

Characterization of Polysorbitol-Based Osmotically Active Transporter/DNA Complex <2-1> DNA Condensation Capability of Polyethyleneimine Copolymer One of the most important features of the gene carrier is to condense a plasmid DNA through interaction. Therefore, DNA condensation capability of the biodegradable polysorbitol-based osmotically active transporter (PSOAT) prepared in Example 1 was examined by agarose gel electrophoresis. First, the PSOAT solution was mixed with pGL3 plasmid (5.3 kb, Promega) at various molar ratios of 0.5, 1, 3, 5 and 10 (N/P ratio), followed by gentle vortexing and incubation at room temperature for 30 minutes. After incubation, each reaction solution was subjected to 1% agarose gel electrophoresis, and DNA migration was observed under UV light. At this time, the pGL3 plasmid alone, which was not reacted with PSOAT of the present invention, was used as a control group.

Figure 3A:
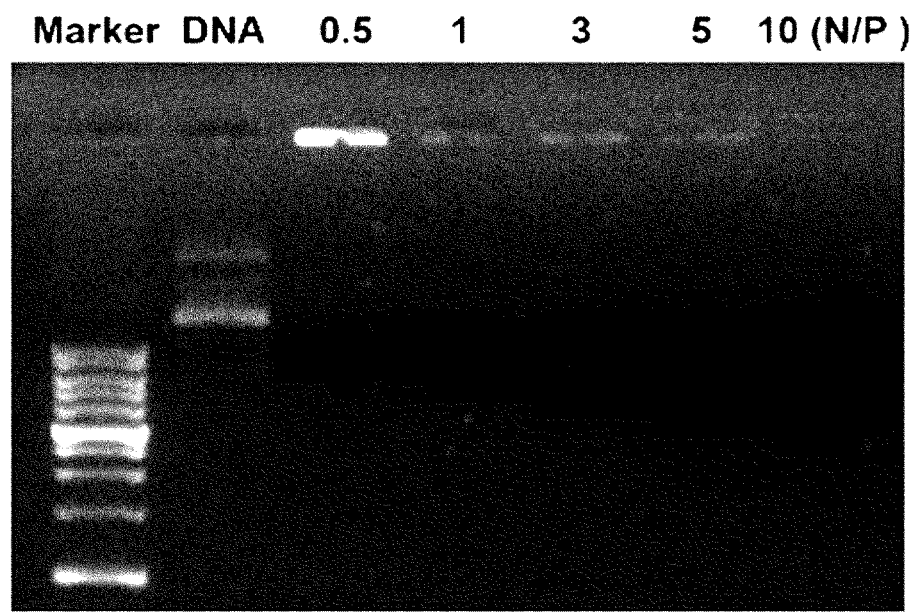
FIG. 3a is the result of agarose gel electrophoresis showing the migration of the gene delivery complexes (PSOAT/DNA) prepared by reacting the polysorbitol-based osmotically active transporter (PSOAT) of the present invention and DNA at various molar ratios.

As shown in FIG. 3a, when the molar ratio of polysorbitol-based osmotically active transporter (PSOAT) of the present invention to the plasmid DNA was 1:0.5 or more, DNA migration was completely delayed, indicating that the polysorbitol-based osmotically active transporter of the present invention effectively condensed plasmid DNA to form a gene delivery complex (PSOAT/DNA). Non-reacted plasmid DNA as the control group migrated through the gel without delay. These results suggest that the plasmid DNA and the polysorbitol-based osmotically active transporter (PSOAT) of the present invention are preferably mixed at a molar ratio of 1:0.5 or more for effective formation of the gene delivery complex.

<2-2> DNA Protection Effect of Polysorbitol-Based Osmotically Active Transporter/DNA Complex For effective gene expression, DNA in the gene delivery complex should be properly protected from enzymatic attack in the body such as nuclease. In order to examine the DNA protection effect, 1 µl of DNase I (2 units) or 1 µl of PBS (phosphate-buffered saline)-containing DNase/$Mg^{2+}$ digestion buffer (50 mM TrisCl, pH 7.6 and 10 mM $MgCl_2$) was added to 4 µl of the gene delivery complex (PSOAT/DNA) solution prepared by reacting the polysorbitol-based osmotically active transporter (PSOAT) and DNA at a molar ratio of 10:1 in Example <2-1> or 4 µl of non-reacted DNA solution, and incubated under stirring at 37° C. and 100 rpm for 30 minutes. To terminate the enzymatic reaction, all reaction solutions were treated with 4 µl of EDTA (250 mM) for 10 minutes, and then mixed with 1% sodium dodecyl sulfate (pH 7.2) to a final volume of 15 µl, followed by incubation at 25° C. for 2 hours. After incubation, the reaction solution was subjected to electrophoresis on a 1% agarose gel using a tris-acetate-EDTA running buffer at 50 V for 1 hour.

Figure 3B:
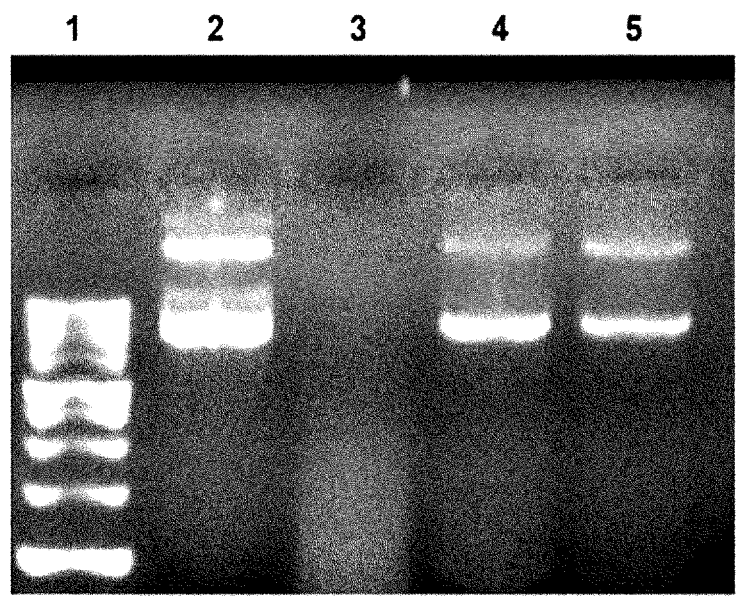
FIG. 3b is the result of showing that the gene delivery complexes (PSOAT/DNA) prepared by reacting the polysorbitol-based osmotically active transporter (PSOAT) of the present invention and DNA at various molar ratios are able to effectively protect DNA from nuclease, in which Lane 1 is a DNA marker, Lane 2 is non-DNase I-treated plasmid DNA (pGL3-control group), Lane 3 is DNase I-treated plasmid DNA (pGL3-control group), Lane 4 is non-DNase I-treated PSOAT/pGL3 complex, and Lane 5 is DNase I-treated PSOAT/pGL3 complex.

As shown in FIG. 3b, the non-reacted plasmid DNA as the control group was completely digested by DNase I (Lane 3), whereas DNA in the gene delivery complex (PSOAT/DNA) of the present invention was effectively protected from DNase I digestion (Lane 6), indicating that the gene delivery complex of the present invention is able to effectively deliver DNA into cells while protecting DNA from nuclease attack.

<2-3> Morphological Analysis of Polysorbitol-Based Osmotically Active Transporter/DNA Complex Morphology of the gene delivery complex (PSOAT/DNA) prepared by reacting the polysorbitol-based osmotically active transporter (PSOAT) and DNA at a molar ratio of 20:1 in Example <2-1> was examined under a transmission electron microscope (TEM) (LIBRA 120, Carl Zeiss, Germany). Morphology of the gene delivery complex (PSOAT/DNA) freeze-dried was also examined under TEM.

Figure 4A:
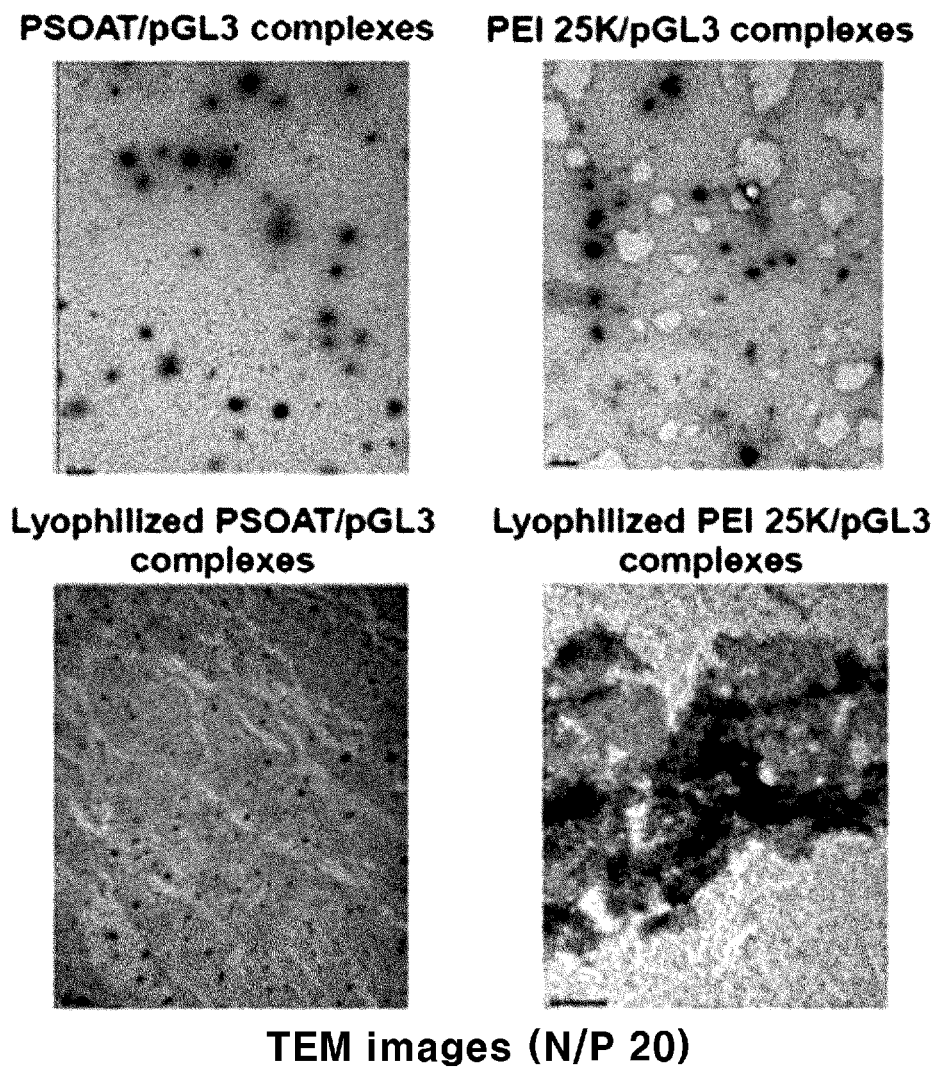
FIG. 4a is the transmission electron microscopic (TEM) images showing the morphologies of the gene delivery complexes (PSOAT/DNA) prepared by reacting the polysorbitol-based osmotically active transporter (PSOAT) of the present invention and DNA at various molar ratios (the bar represents 200 nm)

As shown in FIG. 4a, it was found that the gene delivery complex (PSOAT/DNA) according to the present invention has a uniform spherical compact structure by effective condensation of the polysorbitol-based osmotically active transporter (PSOAT) and plasmid DNA, compared to the PEI 25K/DNA complex used as the control group (upper panel). After freeze-drying, particle agglomeration was caused in the PEI 25K/DNA complex used as the control group, whereas the PSOAT/DNA complex of the present invention maintained structural integrity and stability (lower panel of FIG. 4a), which is attributed to the cryoprotective function of the sorbitol skeleton in the polysorbitol-based osmotically active transporter (PSOAT) according to the present invention.

The particle size of the gene delivery complex is an important factor in access and passage of the complex to the target site and is essential for intracellular influx of the complex. Since most gene delivery complexes are internalized into cells via endocytosis or pinocytosis, the size of complex is required to be smaller than a predetermined size for the optimum intracellular influx. Therefore, the particle sizes of the gene delivery complexes prepared at various molar ratios under serum-free conditions and the gene delivery complexes prepared at a molar ratio of 20:1 in the presence of various concentrations of serum were measured using a dynamic light scattering spectrophotometer (ELS8000, Otsuka Electronics, Osaka, Japan). At this time, the scattering angle was set at 90° and 20°.

Figure 4B:
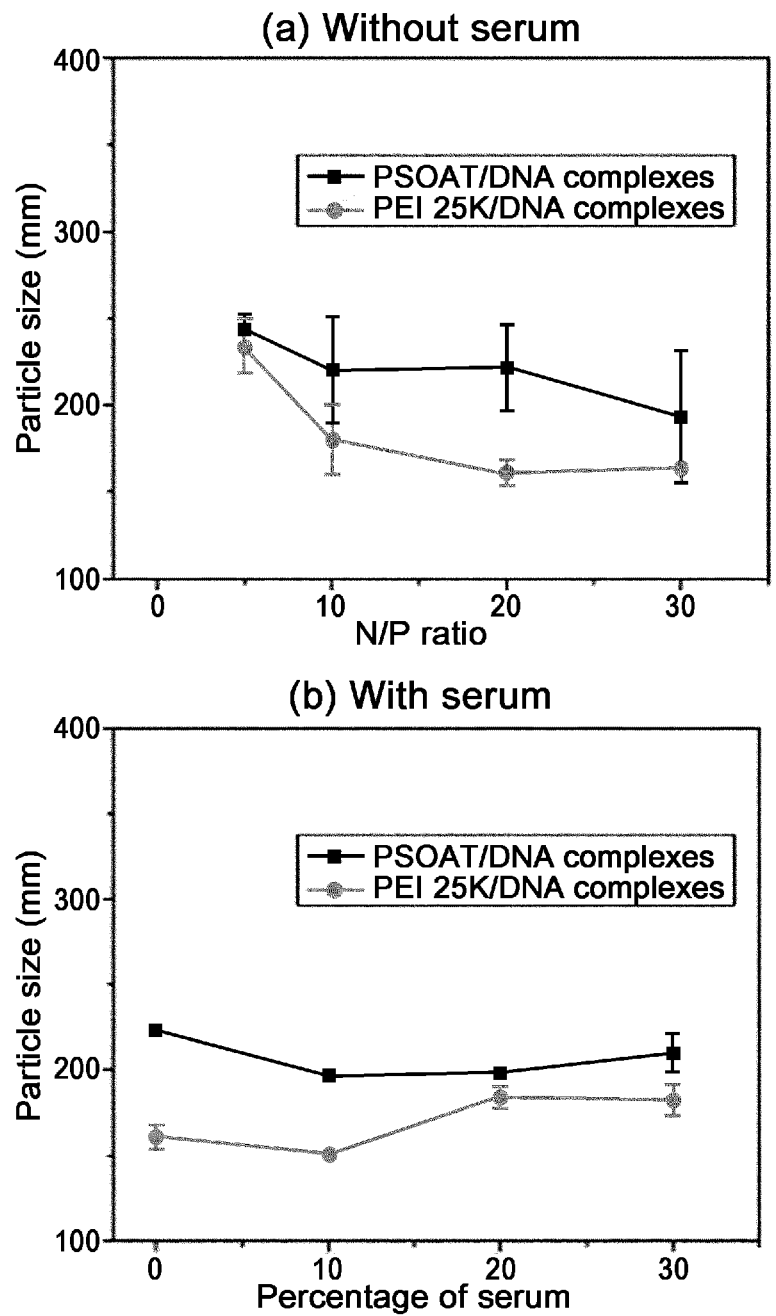
FIG. 4b is the result of analyzing the particle size of the gene delivery complexes (PSOAT/DNA) prepared by reacting the polysorbitol-based osmotically active transporter (PSOAT) of the present invention and DNA at various molar ratios in the presence or absence of serum.

As shown in FIG. 4b, the gene delivery complex (PSOAT/DNA) of the present invention at the molar ratio of 1:1, 10:1, 20:1 and 30:1 showed a relatively uniform particle size distribution of 150 to 250 nm in average (PDI: 2.5e-003) irrespective of presence or absence of serum, indicating that it has a particle size suitable for use as the gene carrier.

<2-4> Measurement of Surface Charge of Polysorbitol-Based Osmotically Active Transporter/DNA Complex The positive surface charge of the gene delivery complex is essential for its binding to the negative cell surface, which facilitates intracellular influx of the complex. Therefore, zeta potentials of the gene delivery complexes (PSOAT/DNA) prepared by reacting the polysorbitol-based osmotically active transporter (PSOAT) of the present invention and plasmid DNA at various molar ratios were measured using a dynamic light scattering spectrophotometer (ELS8000, Otsuka Electronics, Osaka, Japan).

Figure 4C:
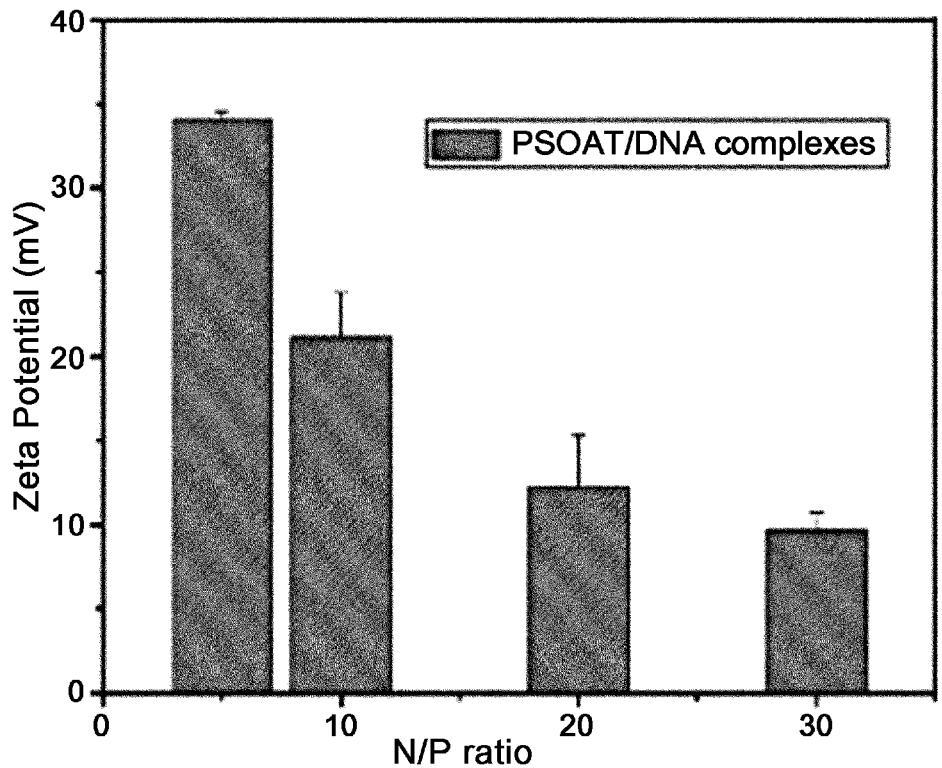
FIG. 4c is the result of measuring the zeta potential of the gene delivery complexes (PSOAT-/DNA) prepared by reacting the polysorbitol-based osmotically active transporter (PSOAT) of the present invention and DNA at various molar ratios.

As shown in FIG. 4c, the gene delivery complex prepared by reacting the polysorbitol-based osmotically active transporter (PSOAT) of the present invention and plasmid DNA at a molar ratio of 5:1 showed the highest positive zeta potential. As the molar ratio increased, the value was decreased, but all positive. The positively charged surface means that negatively charged DNA is completely encapsulated within the gene delivery complex and the positive surface charge facilities intracellular influx of the gene delivery complex and also causes electrical repulsion between particles to reduce their agglomeration.

Example 3

Transfection Efficiency of Polysorbitol-Based Osmotically Active Transporter

<3-1> Analysis of Transfection Efficiency Under Serum-Free Conditions

In order to examine transfection efficiency of the polysorbitol-based osmotically active transporter (PSOAT) of the present invention, in vitro luciferase activity assay was carried out under serum-free conditions.

First, RPMI 1640 (Gibco BRL) medium containing 10% FBS (HyClone), 100 µg/ml streptomycin and 100 U/ml penicillin was added to a 24-well plate, and A549 cells, HeLa cells and H322 cells were seeded at a density of $1.5 \times 10^5$ cells/well and cultured in a 5% $CO_2$ incubator at 37° C. for 18 hours. Furthermore, a pGL3 expression vector (5.3 kb, Promega) containing a luciferase gene, of which expression is induced by SV40 promoter and enhancer, was mixed with the polysorbitol-based osmotically active transporter (PSOAT) solution of the present invention at a molar ratio of 5, 10, 20 and 30, and gently vortexed, followed by incubation at room temperature for 30 minutes to prepare a gene delivery complex (PSOAT/GL3). The medium in the well plate was replaced with a serum-free medium or a medium containing 1 µg of the prepared gene delivery complex (PSOAT/GL3), followed by culture in a 5% $CO_2$ incubator at 37° C. for 4 hours. At this time, the cell culture treated with PEI 25K (25 kDa, Sigma-Aldrich) and Lipofectamine at an equal amount was used as a control group. Thereafter, the medium in the well plate was replaced with a fresh 10% FBS-containing DMEM medium, followed by culture in a 5% $CO_2$ incubator at 37° C. for 48 hours. Subsequently, the medium was removed, and 100 µl of cell lysis buffer was added to each well and left at −20° C. for 24 hours. Then, the culture medium was transferred to an e-tube, and centrifuged at 10,000 rpm for 15 minutes to obtain a supernatant. Luciferase activity of the supernatant thus obtained was measured using a luciferase assay kit (Promega), and its transfection efficiency was expressed as a relative light unit (RLU) per 1 mg of the protein.

Figure 5A:
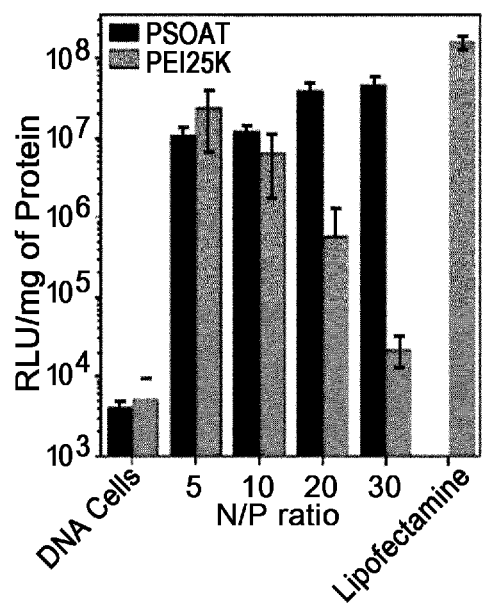
Figure 5B:
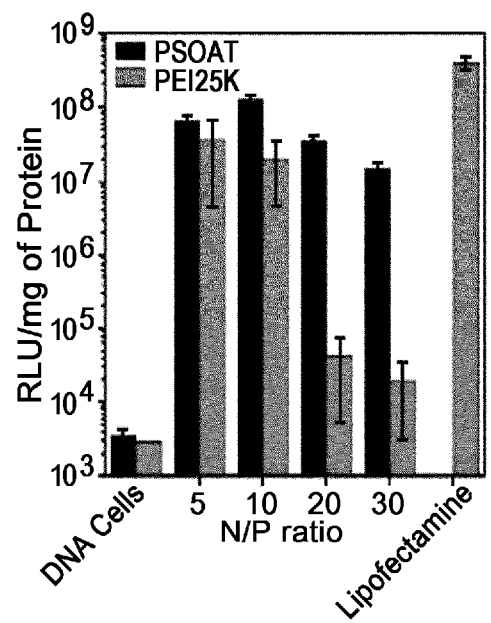
Figure 5C:
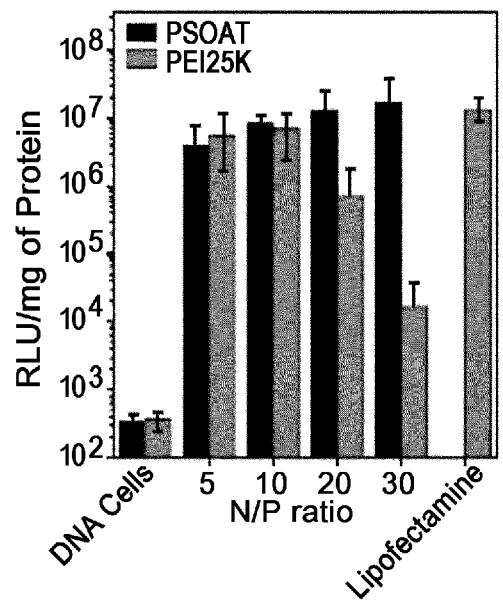

As shown in FIGS. 5a to 5c, as the reaction molar ratio of DNA and PEI 25K was increased, the transfection efficiency of the gene delivery complex was reduced. In contrast, the polysorbitol-based osmotically active transporter (PSOAT) of the present invention showed the transfection efficiency higher than PEI 25K or similar to Lipofectamine even though the reaction molar ratio was increased. These results indicate that the polysorbitol-based osmotically active transporter (PSOAT) of the present invention has excellent DNA binding ability to effectively form a nano-sized gene delivery complex, thereby exhibiting high transfection efficiency. Such high transfection efficiency of the polysorbitol-based osmotically active transporter (PSOAT) according to the present invention is attributed to the buffering capacity of the copolymer.

<3-2> Analysis of Transfection Efficiency in the Presence of Serum

The PSOAT/GL3 complex was prepared in the same manner as in Example <3-1>, except that the reaction molar ratio of the polysorbitol-based osmotically active transporter (PSOAT) of the present invention and pGL3 expression vector was 1:20, and the serum concentration in the medium was 0, 10, 20 and 30%. Then, its Luciferase activity was analyzed.

Figure 6:
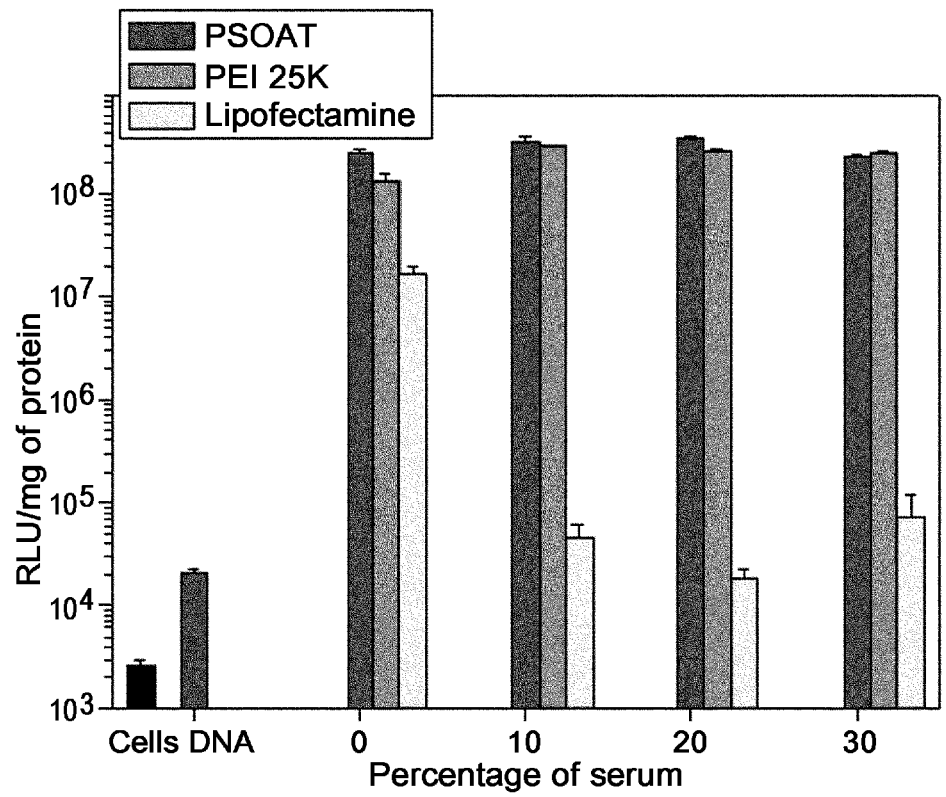
FIG. 6 is the result of analyzing the transfection efficiency of the gene delivery complexes (PSOAT/DNA) prepared by reacting the polysorbitol-based osmotically active transporter (PSOAT) of the present invention and DNA at a molar ratio of 20:1 in HepG2 cell line in presence of serum (n=3, error bars represent standard deviation)

As shown in FIG. 6, the transfection efficiencies of PEI and Lipofectamine were remarkably reduced in the presence of serum, whereas the PSOAT/GL3 complex according to the present invention maintained high transfection efficiency irrespective of serum concentration. When a cationic polymer is used for gene delivery in vivo, its gene delivery complex binds to serum proteins in the blood due to cations, and therefore, the gene delivery complex becomes large, which causes the problem of blood vessel clogging or reduced gene expression efficiency. However, the PSOAT/GL3 complex according to the present invention does not form agglomerates in the presence of serum, and thus it does not cause blood vessel clogging or a reduction in gene expression efficiency.

Example 4

Analysis of Transfection Mechanism of Polysorbitol-Based Osmotically Active Transporter <4-1> Analysis of Buffering Capacity In order to investigate a transfection mechanism of the polysorbitol-based osmotically active transporter (PSOAT) according to the present invention, the buffering capacity of the copolymer was examined. Bafilomycin A1 (specific inhibitor of vacuolar type $H^+$ ATPase, 200 nM) diluted in DMSO was added to A549 cells cultured in the well plate as in Example <3-1> and incubated for 10 minutes, and then the transfection efficiency was measured as above. At this time, the gene delivery complex according to the present invention prepared by reacting DNA and PSOAT at a molar ratio of 1:20 and 1:30 was used, and a gene delivery complex prepared by reacting DNA and PEI 25K at a molar ratio of 1:5 was used as a control group.

Figure 7A:
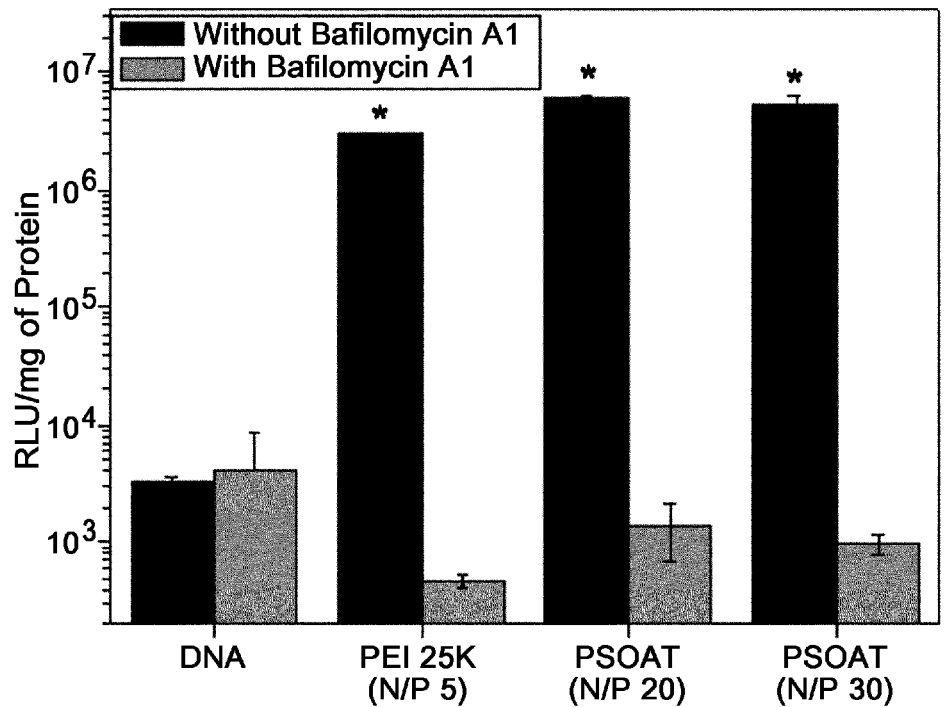
FIG. 7a is the result of analyzing the buffering capacity of the gene delivery complexes (PSOAT/DNA) prepared by reacting the polysorbitol-based osmotically active transporter (PSOAT) of the present invention and DNA at various molar ratios by treatment of bafilomycin A1.

As shown in FIG. 7a, the transfection efficiency of the polysorbitol-based osmotically active transporter (PSOAT) according to the present invention was rapidly reduced after treatment of bafilomycin A1, indicating that PSOAT of the present invention has high buffering capacity, and thus is rapidly released from the endosome by a proton sponge effect and internalized into the cytoplasm.

<4-2> Measurement of Osmotic Activity

The polysorbitol-based osmotically active transporter (PSOAT) of the present invention is a biodegradable gene carrier containing an osmotically active sorbitol skeleton. Therefore, in order to examine the hyperosmotic effect of the polysorbitol-based osmotically active transporter (PSOAT) on the transfection efficiency, changes in packed cell volume (PCV) was measured.

First, 293T cells were suspended in a 10% FBS-containing DMEM medium, and then PSOAT/DNA complexes having different concentrations (0.01, 0.03, 0.05, 1 and 5 wt %) of sorbitol or various contents (0.01, 0.03 and 0.05 wt %) of sorbitol in the polymer skeleton were added thereto. The culture mixture was incubated at 37° C. for 5 minutes, and then the cells were centrifuged for 1 minute in a mini-PCV tube to measure changes in packed cell volume.

Figure 7B:
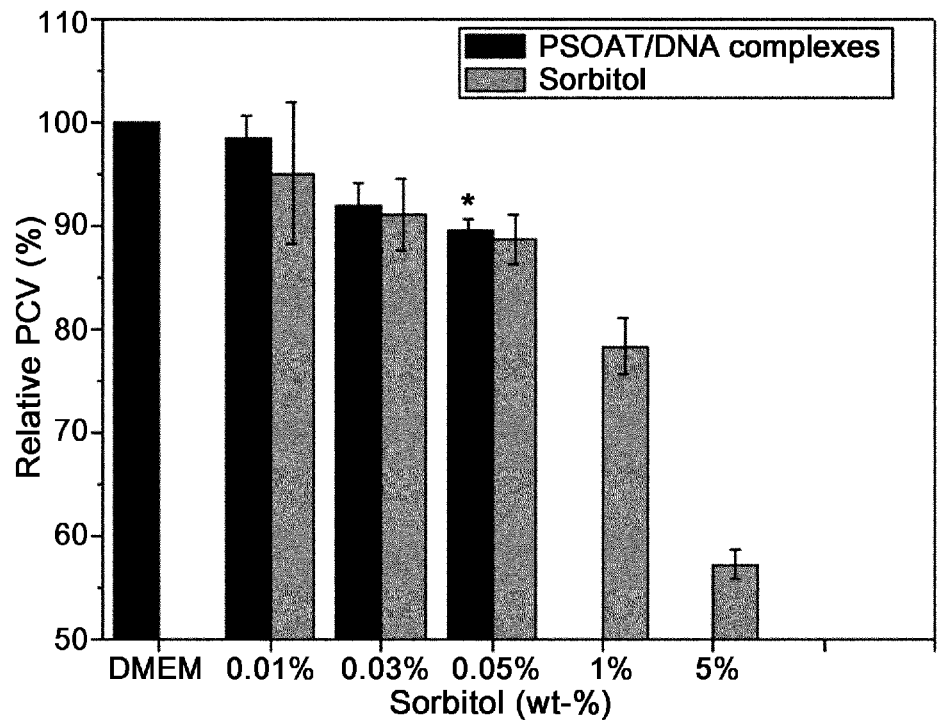
FIG. 7b is the result of analyzing the osmotic activity of the gene delivery complexes (PSOAT/DNA) prepared by reacting the polysorbitol-based osmotically active transporter (PSOAT) of the present invention and DNA at a molar ratio of 20:1 by measuring changes in packed cell volume (PCV)

As shown in FIG. 7b, 20% reduction in PCV was observed in the cells exposed to 1 wt % sorbitol in DMEM. The PSOAT/DNA complexes containing 0.01, 0.03 and 0.05 wt % of sorbitol also reduced PCV in the same manner as in the treatment of pure sorbitol. PCV reduction in the presence of the PSOAT/DNA complex according to the present invention can be understood by the hypothesis that the sorbitol skeleton in PSOAT imparts an osmotic pressure to the cell membrane and makes the cell membrane mild, thereby facilitating cell re-absorption by improved membrane permeability.

<4-3> Examination of Osmotic Activity-Dependent Transfection Efficiency

In order to examine the effect of the osmotic activity on the transfection efficiency of the polysorbitol-based osmotically active transporter (PSOAT) according to the present invention, PSOAT was treated with an osmotic pressure inhibitor, and changes in transfection efficiency were examined.

As the osmotic pressure inhibitor, SC58236 (COX-2 inhibitor, Sigma-Aldrich) preventing organic osmolyte accumulation in the cultured cells was used. First, A549 cells were cultured as in Example <3-1>, and seeded in a 24-well plate at a density of $10 \times 10^4$ cells/well. The medium in the well plate was replaced with a serum-free medium containing 100 µg/ml of PSOAT/GL3 (1:20) and PEI 25K/GL3 (1:5) complex, and the cells were cultured in a 5% $CO_2$ incubator at 37° C. for 24 hours. Subsequently, SC58236 were first dissolved in DMSO and then diluted in the serum-free medium at various concentrations (0, 5, and 30 µM/l), and treated to the well plate. The cells were cultured in a 5% $CO_2$ incubator at 37° C. for 1, 2 and 4 hours. After the medium was removed, 100 µl of cell lysis buffer was added to each well and left at −20° C. for 24 hours. Then, the culture medium was transferred to an e-tube, and centrifuged at 10,000 rpm for 15 minutes to obtain a supernatant. Luciferase activity of the supernatant thus obtained was measured using a luciferase assay kit (Promega), and its transfection efficiency was expressed as a relative light unit (RLU) per 1 mg of the protein.

Figure 8A:
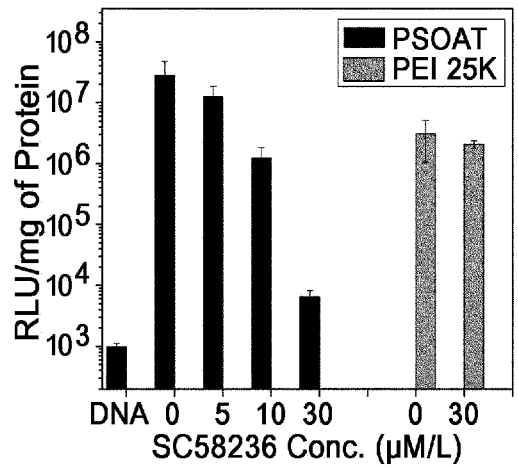
Figure 8B:
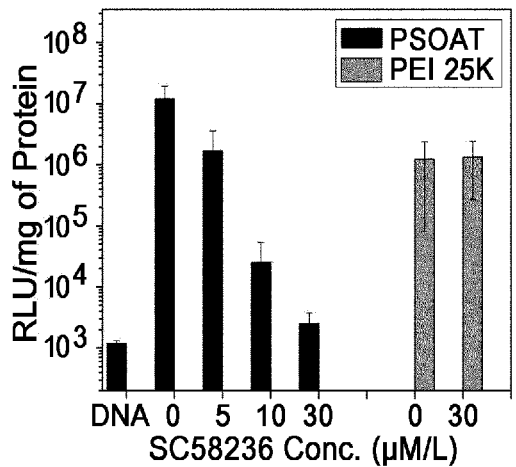
Figure 8C:
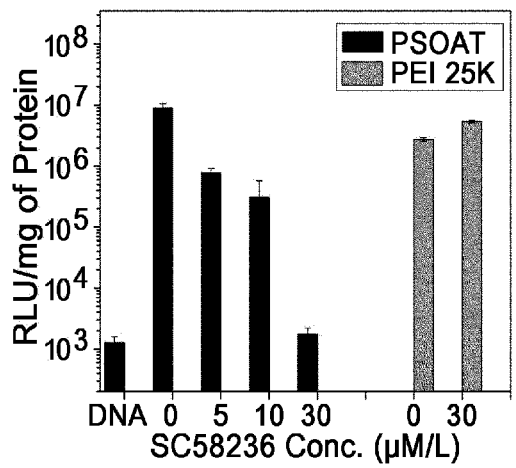

As shown in FIGS. 8a to 8c, as the treatment concentration of the osmotic pressure inhibitor, SC58236 was increased, the transfection efficiency of the polysorbitol-based osmotically active transporter (PSOAT) of the present invention was remarkably reduced. When 30 µM/l of SC58236 was treated, there was no great difference in the transfection efficiency between the PSOAT/GL3 complex according to the present invention and plasmid pGL3 at all analysis time points (after 1, 2 and 4 hours), indicating that the transfection efficiency of PSOAT according to the present invention was completely lost by treatment of the high-concentration osmotic pressure inhibitor. In contrast, the transfection efficiency of PEI 25K was not affected by treatment of the high-concentration osmotic pressure inhibitor at all analysis time points.

These results indicate that the transfection efficiency of the polysorbitol-based osmotically active transporter (PSOAT) of the present invention is attributed to hyperosmotic activity due to the presence of osmotically active sorbitol.

Example 5

Cytotoxicity of Polysorbitol-Based Osmotically Active Transporter

In order to examine cytotoxicity of the polysorbitol-based osmotically active transporter (PSOAT) of the present invention, cells were treated with the gene delivery complexes prepared by reacting DNA and PSOAT at various molar ratios as in Example <3-1>, and then Cell Titer 96 Aqueous One Solution Cell Proliferation Assay was performed to examine cell viability.

First, A549 (human lung adenocarcinoma cell, ATCC) and H322 (human lung cancer cell, ATCC) cells were seeded in an RPMI 1640 (Gibco BRL, Paris, France) medium, and HeLa (human cervical carcinoma cell, ATCC) cells were seeded in a DMEM (Dulbecco's modified Eagle medium, Gibco BRL) medium. The cells were cultured in a 5% $CO_2$ incubator at 37° C. At this time, all media were supplemented with 10% fetal bovine serum (FBS, HyClone, Logan, Utah, USA), 100 µg/ml of streptomycin, and 100 U/ml of penicillin.

The cultured A549, and HeLa and H322 cells were seeded in 96-well plates at a density of $1 \times 10^4$ cells/well, and cultured in a 5% $CO_2$ incubator at 37° C. for 18 hours. The media in the well plates were replaced with the serum-free medium containing the polysorbitol-based osmotically active transporter (PSOAT) of the present invention at a concentration of 5, 10, 20, 50 and 100 µg/ml, and then cultured again in a 5% $CO_2$ incubator at 37° C. for 24 hours. At this time, the cell culture treated with PEI 25K (25 kDa, Sigma-Aldrich) at the same concentration was used as a control group. Thereafter, the medium in the well plate was replaced with a growth medium containing 20 µl of Cell Titer 96 Aqueous One Solution Reagent. After culture for 3 hours, absorbance was measured at 590 nm using an ELISA plate reader (GLR 1000, Genelabs Diagnostics, Singapore) to examine cellular metabolic activity.

Figure 9A:
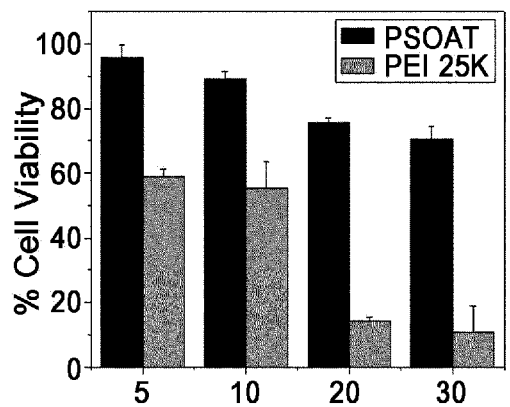
Figure 9B:
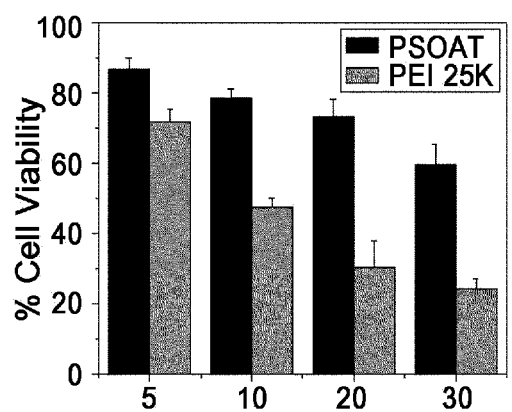
Figure 9C:
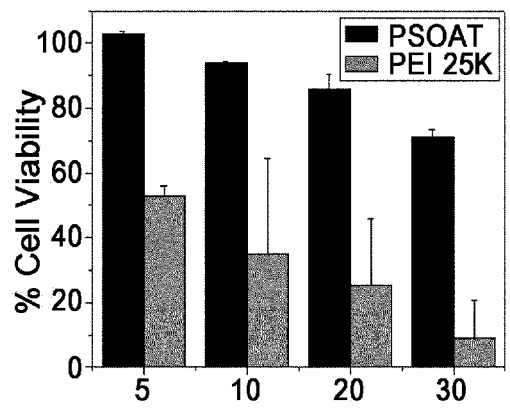
Figure 10:
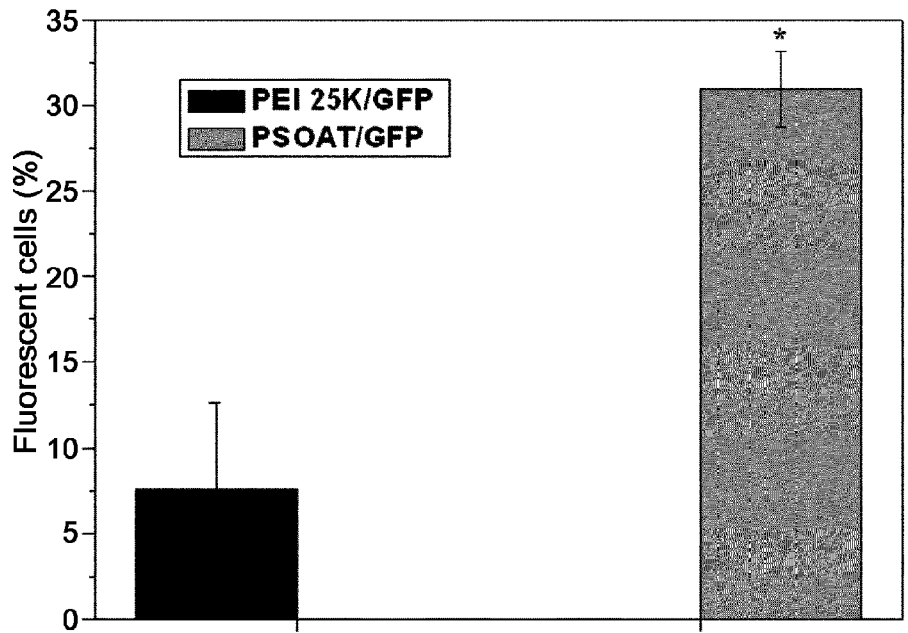
FIG. 10 is the result of flow cytometry for GFP expression after transfection of the gene delivery complexes (PSOAT/GFP) prepared by reacting the polysorbitol-based osmotically active transporter (PSOAT) of the present invention and GFP (green fluorescent protein) at a molar ratio of 20:1 into A549 cells (n=3, error bars represent standard deviation)

As shown in FIGS. 9a to 9c, even though the molar ratio of PSOAT increased (up to 30:1), all cells treated with the PSOAT/DNA complex of the present invention showed 60% or more of cell viability, compared to the control group. In contrast, viability of the cells treated with PEI 25K was rapidly reduced, as the molar ratio of PEI increased. These results indicate that the polysorbitol-based osmotically active transporter (PSOAT) of the present invention shows very low cytotoxicity and excellent biocompatibility.

Example 6

Analysis of In Vitro and In Vivo Transfection Efficiencies of Polysorbitol-Based Osmotically Active Transporter <6-1> Analysis of In Vitro Transfection Efficiency by Flow Cytometry In order to examine in vitro transfection efficiency of the polysorbitol-based osmotically active transporter (PSOAT) of the present invention, GFP expression of PSOAT in 293T cells were analyzed by flow cytometry.

First, the PSOAT of the present invention and a plasmid pcDNA3.1/CT-GFP (6.1 kb, Invitrogen) expressing green fluorescent protein (GFP) were mixed at a molar ratio of 20:1 to prepare a gene delivery complex (PSOAT/GFP). At this time, PEI 25K (25 kDa, Sigma-Aldrich) and the pcDNA3.1/CT-GFP plasmid were mixed at the same molar ratio to prepare a gene delivery complex (PEI 25K/GFP) as a control group. A549 cells were transfected with PSOAT/GFP and PEI 25K/GFP complexes, respectively and then washed with PBS, followed by trypsin treatment. A ratio (%) of GFP expressed from the cells was recorded using a FACS Calibur System (Becton-Dickinson, San Jose, Calif.) to evaluate transfection efficiency. This experiment was repeated three times and 20 cells were counted at each experiment.

As shown in FIG. 9, only approximately 15% cells of the PEI 25K/GFP complex-treated group were fluorescent cells, whereas approximately 30% cells or more of the PSOAT/GFP complex-treated group were fluorescent cells, indicating that the PSOAT of the present invention exhibits more excellent transfection efficiency than PEI 25K.

<6-2> Analysis of In Vivo Transfection Efficiency by Aerosol Delivery

In order to examine in vivo transfection efficiency of the polysorbitol-based osmotically active transporter (PSOAT) of the present invention by aerosol delivery, the following experiment was performed.

First, the polysorbitol-based osmotically active transporter (PSOAT) and the plasmid pcDNA3.1/CT-GFP (6.1 kb, Invitrogen) expressing GFP were mixed at a molar ratio of 20:1 to prepare a gene delivery complex (PSOAT/GFP) as in Example <6-1>.

6-week-old male C57BL/6 mouse (Breeding and Research Center) were maintained at a temperature of 23±2° C. and a relative humidity of 50±20% with a 12-hr night/day cycle in the animal facility. All protocols of this experiment were approved by Animal Care and Use Committee at Seoul National University (SNU-101211-2). In order to examine gene transfer efficiency via aerosol, a nose-only exposure chamber (NOEC; Dusturbo, Seoul, Korea) was used, and 4 mice were randomly divided into two groups (2 mice per group) as follows: PEI 25K/GFP complex-treated group; and PSOAT/GFP complex-treated group. To deliver 1 mg of DNA to the mice of each group, mice were exposed to aerosol according to the method used in the literature (H. L. Jiang et al., Biomaterials 30: 5844-5852, 2009).

2 days after aerosol exposure, mice of each group were sacrificed and the lungs were removed. The lungs were fixed in 4% paraformaldehyde for 12 hours, and then dipped in a 30% sucrose solution, and stored at 4° C. for 48 hours. The fixed lungs were embedded in OCT compound (Tissue-Tek OCT, Sakura) at a temperature of −20° C. or below, and then cut using a microtome to prepare lung tissue sections having a thickness of 10 μm. For histopathological analysis, the prepared lung tissue sections were stained with hematoxylin and eosin (H&E), and GFP signals were observed under a confocal microscope (Zeiss LSM510, Carl Zeiss).

Figure 11:
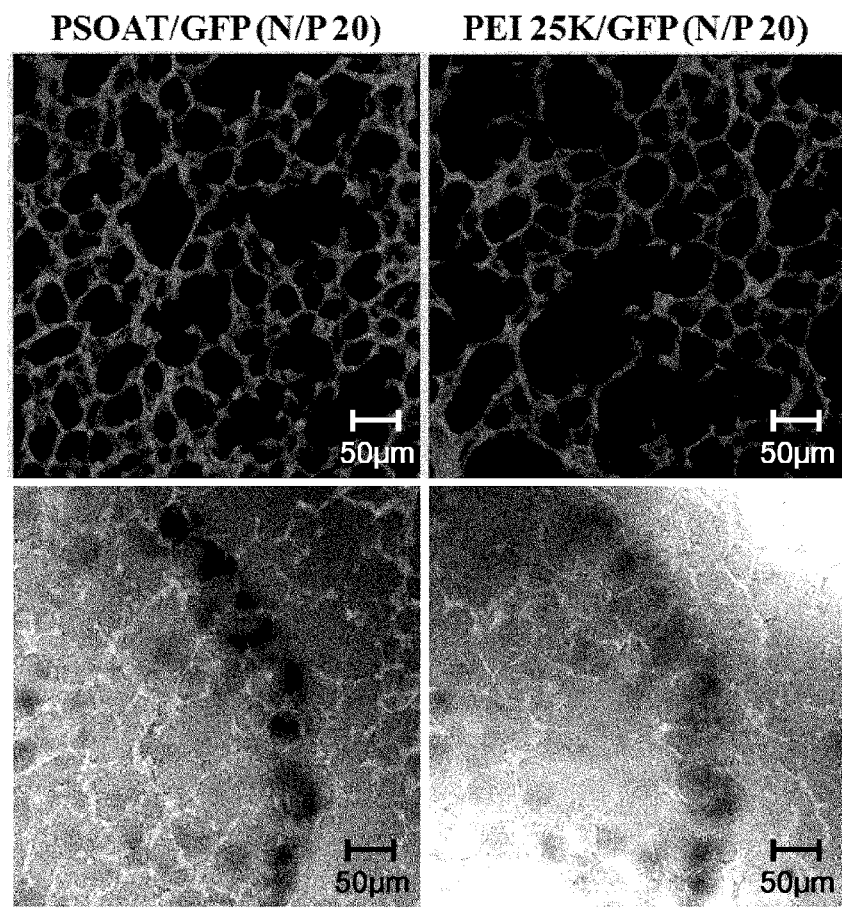
FIG. 11 is the result of analyzing GFP expression in vivo after administration of the gene delivery complexes (PSOAT/GFP) prepared by reacting the polysorbitol-based osmotically active transporter (PSOAT) of the present invention and GFP (green fluorescent protein) at a molar ratio of 20:1 to the lungs of mice via aerosol (magnification: 200×, the scale bars represent 50 μm).

As shown in FIG. 11, stronger GFP signals were detected in the group treated with the PSOAT/GFP complex of the present invention than in the group treated with PEI 25K/GFP complex, indicating very excellent aerosol delivery efficiency.

INDUSTRIAL APPLICABILITY

The biodegradable polysorbitol-based osmotically active transporter (PSOAT) of the present invention includes an osmotically active sorbitol skeleton, which imparts an osmotic pressure to the cell membrane to improve membrane permeability, thereby facilitating cell re-absorption, and thus it exhibits remarkably improved transfection efficiency. Further, the polysorbitol-based osmotically active transporter (PSOAT) of the present invention exhibits high DNA binding ability, effectively protects DNA from nuclease, exhibits physicochemical properties suitable for use as a gene carrier, and has very low cytotoxicity in vitro and in vivo, thereby being useful as a gene carrier for gene therapy.

The invention claimed is:

1. A biodegradable polysorbitol-based osmotically active transporter (PSOAT) which is a copolymer of polyethyleneimine (PEI) and a sorbitol-based derivative.

2. The biodegradable polysorbitol-based osmotically active transporter (PSOAT) according to claim 1, wherein the polyethyleneimine (PEI) is linear or branched, and has a molecular weight ranging from 50 to 10,000 Da.

3. The biodegradable polysorbitol-based osmotically active transporter (PSOAT) according to claim 1, wherein the sorbitol-based derivative is selected from the group consisting of sorbitol diacrylate (SDA), sorbitol dimethacrylate (SDM), sorbitol triacrylate (STA), sorbitol trimethacrylate (STM), sorbitol tetracrylate (STEA), sorbitol tetramethacrylate (STEM), sorbitol pentacrylate (SPA) and sorbitol petamethacrylate (SPM).

4. The biodegradable polysorbitol-based osmotically active transporter (PSOAT) according to claim 3, wherein the sorbitol-based derivative is sorbitol dimethacrylate (SDM) represented by the following Chemical Formula 3:

5. The biodegradable polysorbitol-based osmotically active transporter (PSOAT) according to claim 1, wherein the transporter is represented by the following Chemical Formula 4:

wherein x is an integer of 1 to 200, and n is an integer of 1 to 500.

6. The biodegradable polysorbitol-based osmotically active transporter (PSOAT) according to claim 1, wherein the transporter has a molecular weight ranging from 1,000 to 100,000 Da.

7. A method for preparing the biodegradable polysorbitol-based osmotically active transporter (PSOAT) of claim 1, the method comprising the steps of:
   1) dissolving a sorbitol-based derivative and polyethyleneimine (PEI) in reaction solvents to form a polyethyleneimine solution and a sorbitol-based derivative solution, respectively;
   2) adding the polyethyleneimine (PEI) solution to the sorbitol-based derivative solution to perform Michael addition; and
   3) separating a copolymer formed from the reactants.

8. The method according to claim 7, wherein the reaction solvent in step 1) is selected from the group consisting of dimethyl sulfoxide, methyl alcohol anhydrous, ethylalcohol, dimethylformamide, and dioxane.

9. The method according to claim 7, wherein Michael addition in step 2) is performed at 40 to 100° C. for 1 to 24 hours.

10. The method according to claim 7, wherein the polyethyleneimine (PEI) and the sorbitol-based derivative in step 2) have a reaction molar ratio (N/P ratio) ranging from 1:0.1 to 1:10.

11. A gene delivery complex that is prepared by binding a therapeutic gene to the biodegradable polysorbitol-based osmotically active transporter (PSOAT) claim 1.

12. The gene delivery complex according to claim 11, wherein the therapeutic gene and the biodegradable polysorbitol-based osmotically active transporter (PSOAT) bind to each other at a molar ratio of 1:0.5 to 1:100.

13. The gene delivery complex according to claim 11, wherein the therapeutic gene is selected from the group consisting of DNA, single-stranded RNA, double-stranded RNA, lysozyme, DNA-RNA hybrid, and antisense DNA.

14. The gene delivery complex according to claim 13, wherein the therapeutic gene is siRNA or antisense oligonucleotide.

15. The gene delivery complex according to claim 11, wherein the gene delivery complex has an average particle size of 150 to 250 nm.

16. The gene delivery complex according to claim 11, wherein the gene delivery complex shows a zeta potential ranging from 1 to 50 mV.

17. A pharmaceutical composition for gene therapy comprising the gene delivery complex of claim 11 as an active ingredient.

18. The pharmaceutical composition according to claim 17, wherein the pharmaceutical composition is formulated to deliver the gene delivery complex to a target site via aerosol delivery.

19. A method for preventing or treating therapeutic gene-related disease or symptoms, the method comprising the step of administering a therapeutically effective amount of the gene delivery complex of claim 11 to a subject in need thereof, wherein the gene delivery complex is prepared by binding a therapeutic gene to a biodegradable polysorbitol-based osmotically active transporter (PSOAT).

20. The method according to claim 19, wherein the administration is carried out via aerosol delivery.

21. A copolymer of polyethyleneimine (PEI) and a sorbitol-based derivative, which is represented by the following Chemical Formula 4:

wherein x is an integer of 1 to 200, and n is an integer of 1 to 500.

* * * * *